US006234001B1

(12) United States Patent
Sorensen et al.

(10) Patent No.: US 6,234,001 B1
(45) Date of Patent: May 22, 2001

(54) APPARATUS AND METHOD FOR GENERATING CALIBRATION GAS

(76) Inventors: Ian W. Sorensen, 5337 N. Questa Tierra Dr., Phoenix, AZ (US) 85012; Edward A. Lamb, 5102 S. Fern Ct., Chandler, AZ (US) 85248

( * ) Notice: Subject to any disclaimer, the term of this patent is extended or adjusted under 35 U.S.C. 154(b) by 0 days.

(21) Appl. No.: 09/368,022

(22) Filed: Aug. 3, 1999

(51) Int. Cl.[7] ................................................. G01N 31/00
(52) U.S. Cl. .............................................................. 73/1.04
(58) Field of Search ................................... 73/1.02–1.07

(56) References Cited

U.S. PATENT DOCUMENTS

| 3,614,855 | * 10/1971 | Van Luik, Jr. ........................ 73/1.04 |
| 4,069,701 | 1/1978 | Baldauf et al. . |
| 4,164,861 | * 8/1979 | Schlereth et al. ..................... 73/1.04 |
| 4,269,057 | 5/1981 | Ong et al. . |
| 4,723,436 | 2/1988 | Moreth et al. . |
| 5,452,600 | 9/1995 | Davies et al. . |
| 5,457,983 | 10/1995 | Sauvageau et al. . |
| 5,493,891 | 2/1996 | Slemeyer . |
| 5,616,822 | 4/1997 | Griffiths et al. . |

FOREIGN PATENT DOCUMENTS 2 212 610 * 7/1989 (GB) ..................................... 356/440

* cited by examiner

Primary Examiner—Robert Raevis
(74) Attorney, Agent, or Firm—Parsons & Goltry; Robert A. Parsons; Michael W. Goltry

(57) ABSTRACT

Apparatus for generating calibration gas comprising a contained stream of carrier gas, and a chamber containing at least part of the stream and a volatile reference liquid held by a wick structure so that as the stream passes through the chamber, the volatile reference liquid evaporates from the wick structure into a gas that blends into the carrier gas to form a calibration gas.

25 Claims, 1 Drawing Sheet

APPARATUS AND METHOD FOR GENERATING CALIBRATION GAS

FIELD OF THE INVENTION

This invention concerns improved apparatus and methods for generating calibration gas.

BACKGROUND OF THE INVENTION

Most gas analyzers require periodic calibration to ensure proper performance. A typical calibration process consists of feeding a calibration gas into the inlet of a gas analyzer. The concentration of calibration gas can range from parts per billion (ppb) to parts per million (ppm) and higher.

Calibration gas can be purchased compressed in large, heavy cylinders or tanks. Because most calibration gases are volatile, tanks of compressed calibration gas are inherently dangerous. For field use, smaller and often disposable cylinders are available, but these cylinders are expensive and the quantity of contained gas comparatively small. Cylinders of calibration gas also have a limited shelf life depending on the gas composition and concentration.

As an alternative to purchasing cylinders of compressed calibration gas, permeation devices can be used. A typical permeation device comprises a small container of a highly concentrated calibration gas, usually in liquid form. Part of the container consists of a permeable material that permits molecules of the gas to pass through at a controlled rate. This rate is extremely temperature dependent. Therefore, for a constant emission, the permeation device is usually maintained in a temperature controlled oven. A carrier gas can be moved past the permeation device to produce a blended concentration of the calibration gas. Such systems are not available for all calibration gases and the temperature control issue is problematic for field use. Even in the laboratory, stabilization of a permeation system can take a considerable amount of time and effort. Furthermore, permeation devices cannot be turned off, although refrigeration can slow the emission to a level low enough to assure a reasonable shelf life.

Electrochemical cells can also be used to produce a controlled quantity of calibration gas. Although electrochemical cells stabilize quickly and are available in compact packages, they cannot be used with ammonia and other important calibration gases, and replacement cells are costly.

In view of these and other deficiencies in the art, it would be highly desirable to provide new and improved apparatus and methods for generating calibration gas.

Accordingly, it is a purpose of the invention to provide new and improved apparatus for generating calibration gas that is easy to construct.

It is another purpose of the invention to provide new and improved apparatus for generating calibration gas that is easy to use.

It is still another purpose of the invention to provide new and improved apparatus for generating calibration gas that is inexpensive.

It is a further provision of the invention to provide new and improved apparatus for generating calibration gas that uses low-cost consumables.

It is still a further provision of the invention to provide new and improved apparatus for generating calibration gas that is not temperature dependent.

It is yet still a further purpose of the invention to provide new and improved apparatus for generating calibration gas that is lightweight and portable.

It is yet a further purpose of the invention to provide new and improved apparatus for generating calibration gas that is neither chemically nor physically hazardous.

It is another purpose of the invention to provide new and improved apparatus for generating calibration gas that provides a wide range of calibration gas concentrations.

SUMMARY OF THE INVENTION

The above problems and others are at least partially solved and the above purposes and others realized in new and improved apparatus for generating calibration gas comprising a structure for containing a stream of carrier gas, a chamber coupled to the structure for containing at least part of the stream, and a wick structure contained in the chamber for receiving and holding a volatile reference liquid that, when exposed to a stream of carrier gas, evaporates from the wick structure into a gas that blends into the carrier gas to form a calibration gas. A source of volatile reference liquid is preferably coupled with the wick structure in liquid communication. A pump transfers the volatile reference liquid from the source to the wick structure at a desired flow rate and is adjustable for varying the flow rate of the volatile reference liquid. Another pump is also coupled to the structure for providing a stream of carrier gas through the structure at a desired flow rate. The other pump is also adjustable for varying the flow rate of the stream. By varying the flow rate of the stream and/or the volatile reference liquid, the concentration of volatile reference gas in the calibration gas can be specifically and efficiently controlled. A baffle chamber may be coupled to the structure for receiving and mixing the calibration gas to rid it substantially of volatile reference gas concentration irregularities.

The wick structure is preferably constructed of a porous high surface area media and comprises a stage and a wick element. The stage is preferably engaged directly to the wick element and functions to receive the volatile reference liquid from the source and conduct it evenly to the wick element. The wick element is preferably elongate and tubular for providing a large evaporative surface area.

Consistent with the foregoing, the invention also provides associated methods of generating a calibration gas.

BRIEF DESCRIPTION OF THE DRAWINGS

The foregoing and further and more specific objects and advantages of the invention will become readily apparent to those skilled in the art from the following detailed description thereof taken in conjunction with the drawings in which.

DETAILED DESCRIPTION OF PREFERRED EMBODIMENTS

Figure 1:
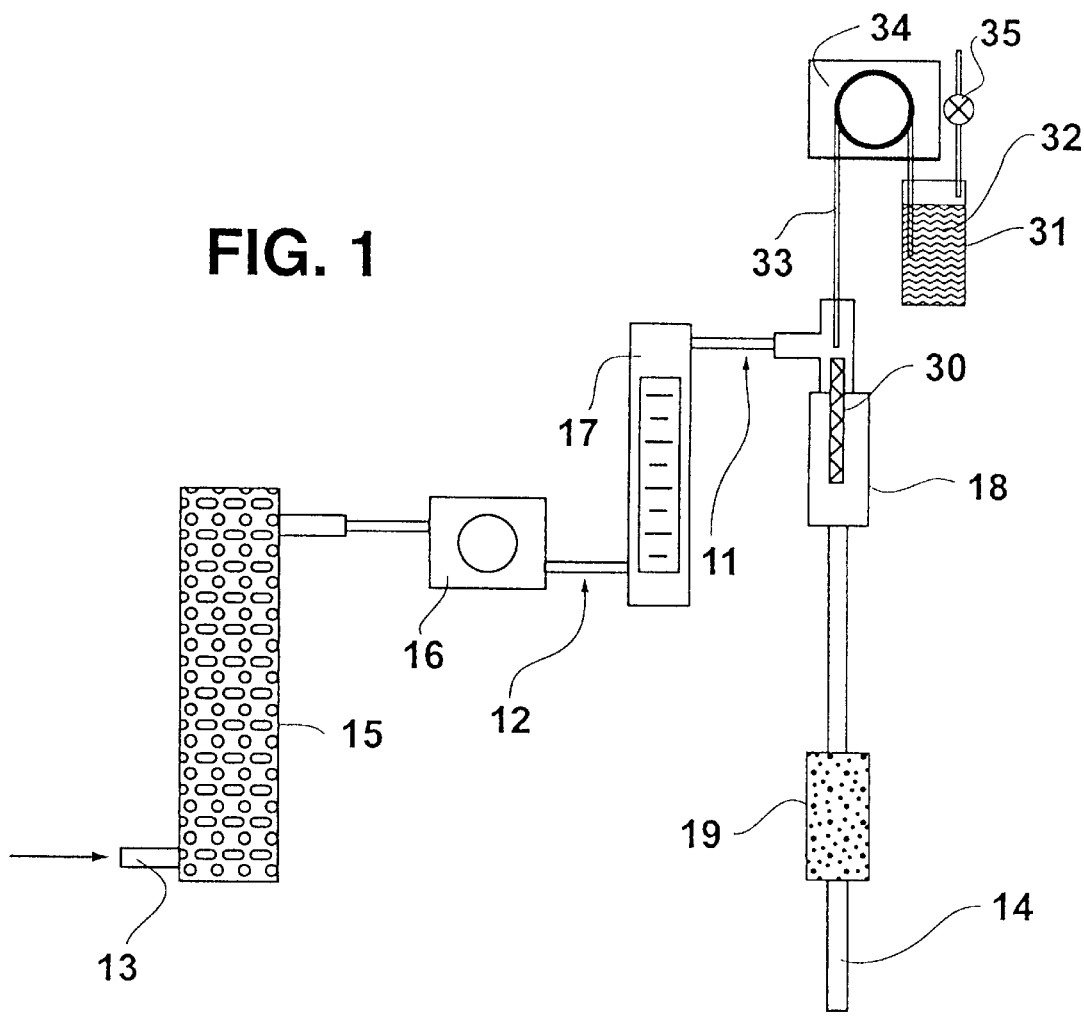
FIG. 1 is a schematic view of apparatus for generating calibration gas comprising a structure for containing a stream of carrier gas, a chamber coupled to the structure for containing at least part of the stream, and a wick structure contained in the chamber for receiving and holding a volatile reference liquid that, when exposed to a stream of carrier gas, evaporates from the wick structure into a gas that blends into the carrier gas to form a calibration gas.

Turning to the drawings, in which like reference characters indicate corresponding elements throughout the several views, FIG. 1 is a schematic view of apparatus 10 for generating calibration gas for use in calibrating gas analyzers in, for example, atmospheric monitors, breath analyzers, toxic and/or odoriferous gas detectors and other instruments or devices having gas analyzers that require periodic or continuous calibration. Apparatus 10 comprises a structure 11 for containing a stream of carrier gas. In this embodiment, structure 11 comprises a conduit structure or arrangement 12 to which the various elements of the invention are associated to interact with the stream. Conduit structure 12 defines an inlet 13 for receiving carrier gas and an outlet 14 for emitting calibration gas, and may be provided in the form of piping or interconnected pipe segments constructed of non-reactive materials such as polyvinyl chloride, stainless steel, polytetrafluoroethylene (PTFE), etc. In operation, the stream of carrier gas flows through conduit structure 12 from inlet 13 to outlet 14. Accordingly, inlet 13 defines the upstream end of the stream and outlet 14 defines the downstream end of the stream.

Coupled to conduit structure 12 in series from inlet 13 to outlet 14 is a desiccant column 15 for thoroughly drying the stream of carrier gas, a pump 16 for creating and driving the stream of carrier gas through the conduit structure 12, a flow meter 17 for measuring the flow rate of the stream of carrier gas as provided by pump 16, a chamber 18 for introducing reference gas into the carrier gas to create a calibration gas, and a baffle or mixing chamber 19 for mixing the calibration gas to rid it of any reference gas concentration irregularities. Desiccant column 15 is a conventional device of a type found under the exemplary trademark DRIERITE TM. Depending on specific user needs, other conventional desiccant apparatus may be used as required. The drying of the stream of carrier gas is important because it ensures that the carrier gas stream will have sufficient capacity for absorbing the reference gas in chamber 18. Pump 16 is preferably electrically powered, and may comprise any conventional and readily available pump constructed to pump air or gas. Like many conventional air or gas pumps, pump 16 is preferably adjustable for allowing the flow rate of the stream of carrier gas to be adjusted. Flow meter 17 is also conventional and may comprise one or more of a variety of well-known and readily available devices operative for measuring the flow rate of air or gas. Rather than, or in addition to, an adjustable pump, flow meter 17 may also be adjustable for adjusting the flow rate of the carrier gas stream.

In the preferred embodiment shown in FIG. 1, desiccant column 15 is the first component along conduit structure 12. Although desiccant column 15 could be located elsewhere along conduit structure 12, it must be located at least upstream of chamber 18 so that as the carrier gas passes through chamber 18, it has sufficient capacity to accommodate a reference gas. The preferable location of pump 16 and flow meter 17 is also upstream of chamber 18. Flow meter 17 may be positioned either downstream of pump 16 as shown, or upstream if so desired. It is preferable to locate flow meter 17 directly adjacent pump 16 which allows it to accurately measure the flow rate of the stream of carrier gas as provided by pump 16. Nevertheless, flow meter 17 need not necessarily be located directly adjacent pump 16, and can otherwise be located anywhere along the length of conduit structure 12 upstream of chamber 18.

In operation, pump 16 draws carrier gas into the desiccant column 15 from the inlet 13 and pumps it into chamber 18. The carrier gas could comprise clean air or gas, or perhaps odoriferous, toxic or contaminated air or gas passing through a scrubber apparatus or other gas or air treatment device. Chamber 18 receives and contains part of the stream of the carrier gas between inlet 13 and outlet 14. Chamber 18 also contains a wick structure 30 that holds a volatile reference liquid. Wick structure 30 is coupled in liquid communication with a source 31 of a volatile reference liquid 32 by way of a liquid conduit 33. Volatile reference liquid 32 may comprise ammonia, hydrogen chloride, hydrogen fluoride, or solutions thereof, etc. Liquid conduit 33 extends from wick structure 30 outwardly through conduit structure 12 and terminates with source 31. A pump 34 is coupled to liquid conduit 33. Pump 34 is preferably electrically powered, and may comprise a peristaltic pump or any other conventional and readily available pump designed to pump liquid. Like many conventional liquid pumps, pump 34 is preferably adjustable for allowing the flow rate of the volatile reference liquid 32 through liquid conduit 33 to be adjusted and controlled. A liquid flow meter may be coupled to liquid conduit 33 for measuring the flow rate of the volatile reference liquid 32 if desired. As the stream of carrier gas passes through chamber 18, the volatile reference liquid 32 evaporates from wick structure 30 into a volatile reference gas that blends into the carrier gas to form a calibration gas. Wick structure 30, therefore, meters reference gas into chamber 18 for absorption into the carrier gas stream. The metering of the reference gas from wick structure 30 is dependent directly upon the flow rate of the volatile reference liquid into wick structure 30. From chamber 18, the calibration gas passes into baffle chamber 19 which receives and mixes the calibration gas to rid it substantially of any volatile reference gas concentration irregularities.

The concentration of volatile reference gas in the calibration gas is inversely related to the flow rate of the carrier gas passing through chamber 18. If the flow rate of the carrier gas is slow through chamber 18, it will linger in chamber 18 which allows a larger amount of volatile reference gas to mingle with a given volume of the carrier gas. As the flow rate of the carrier gas increases through the chamber 18, it will linger less in chamber 18 so lesser amounts of volatile reference gas will mingle with a given volume of carrier gas. Depending on a desired concentration of calibration gas, control of the flow rate of the carrier gas through conduit structure 12 is, therefore, important as it provides a means to maintain a desired final concentration. A user may, of course, control the operation of pump 16 either manually or with controls.

Wick structure 30 is constructed of a non-reactive, porous high surface area media that wets easily such as ceramic braid or other similar material. The volatile reference liquid 32 is pumped through the liquid conduit 33 with pump 34 that draws from source 31. Source 31 comprises a receptacle which is sealed from the atmosphere except for a venting valve 35 which provides pressure equalization during pump 34 operations. As the volatile reference liquid exits liquid conduit 33 and passes into wick structure 30, it disperses quickly and completely evaporates into the passing stream of carrier gas which forms the calibration gas. Regardless of the flow rate of the carrier gas, the concentration of volatile reference gas in the calibration gas becomes constant after about only 100 seconds. Obviously, this stabilization period depends on the time required for volatile reference liquid 32 to be pulled from source 31. However, after the calibration gas concentration stabilizes, changes in the flow rate of the volatile reference liquid 32 become manifest very quickly in the calibration gas concentration. By adjusting the flow rate of volatile reference liquid 32 with pump 34, the calibration gas concentration may be varied very quickly and efficiently. As the skilled artisan might expect, the calibration gas concentration is proportional to the flow rate of the volatile reference liquid 32 to wick structure 30. Furthermore, because the pumping speed of pump 34 is controllable, the calibration gas concentration may be varied without altering the flow rate of the carrier gas, which is important for applications that require a specific calibration gas flow rate for calibration.

Figure 2:
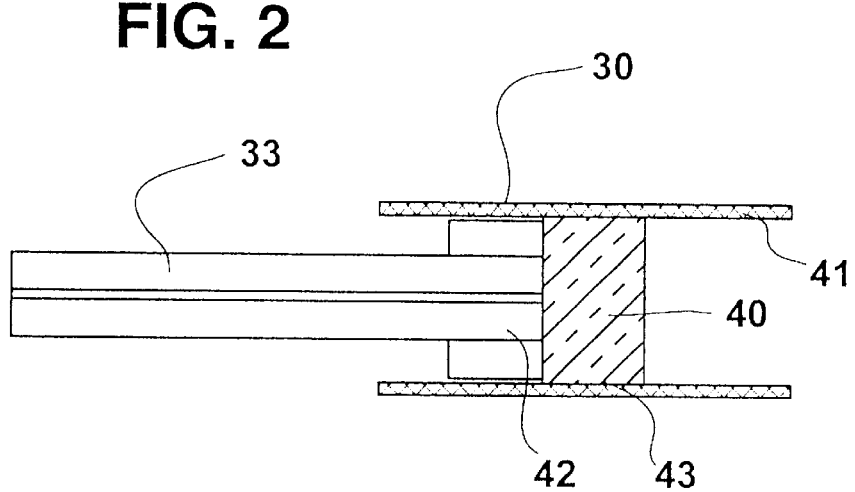
FIG. 2 is a sectional view of the wick of FIG. 1.

As previously mentioned, wick structure 30 is constructed of a porous high surface area media. Turning to FIG. 2, wick structure is comprised of a stage 40 and a wick element 41. An outlet end 42 of liquid conduit 33 abuts or otherwise directly engages stage 40. Stage 40 defines an outer perimeter 43 engaged directly to or against wick element 41. Wick element 41 is elongate and tubular which presents a large surface area to the passing stream of carrier gas. This provides for rapid vaporization of the volatile reference liquid 32 into the passing stream of carrier gas. As volatile reference liquid 32 emerges from outlet end 42, it passes directly into stage 40. Because stage 40 is constructed of a porous high surface area media, the volatile reference liquid rapidly disperses throughout stage 40 and, because it is engaged directly to or against wick element 41, conducts evenly into wick element 41 from stage's 40 outer perimeter 43. Therefore, stage 40 operates to receive the volatile reference liquid 32 and conduct it rapidly and evenly to wick element 41. The architecture of wick structure 30 provides a continuous path for volatile reference liquid 32 to follow from the outlet end 42 of liquid conduit 33 to wick element 41. This eliminates any and all "droplet" formation and, therefore, the possibility of volatile reference liquid 32 entering wick element 41 in pulses or waves.

In summary, the present invention provides new and improved apparatus and associated methods of generating a calibration gas. The apparatus 10 of the invention may be constructed of varying size, and may be constructed and arranged to be portable with batteries for driving pumps 16 and 34. A control panel having switches for power, carrier gas flow and volatile reference liquid flow may be incorporated with the invention. The control panel may include one or more processors that may be programmed for offering, for instance, a "prime" operation mode that speeds pump 34 when it is first turned on. This brings fresh volatile reference liquid 32 from source 31 to chamber 18 quickly and reduces the stabilization time. Furthermore, as a result of the arrangement of chamber 18 and wick structure 30, exposure of apparatus 10 to temperature fluctuations results in little if any variations in calibration gas concentrations. As long as the carrier gas is dry enough to have sufficient capacity to absorb the reference gas being metered or presented from wick structure 30 into chamber 18, temperature will have a negligible impact on the concentration of the calibration gas. Furthermore, the combination of pump 34 to pump controlled amounts of reference liquid, and a sufficiently dry calibration gas stream allows the skilled artisan to produce a very controlled and accurate concentration of calibration gas, and ensures that all of the reference gas metered from wick structure 30 evaporates into the carrier gas stream. As a result of the architecture of this invention, the skilled artisan need not worry about the partial pressure, the solution activity coefficient or other physical properties of the volatile reference liquid.

The present invention has been described above with reference to a preferred embodiment. However, those skilled in the art will recognize that changes and modifications may be made in the described embodiments without departing from the nature and scope of the present invention. Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. Apparatus for generating calibration gas comprising:
   a structure for providing a stream of carrier gas, the structure having a chamber containing a porous high surface area media; and
   a pump for pumping volatile reference liquid from a source to the media which evaporates therefrom into a reference gas that the stream of carrier gas passing through the chamber absorbs to form a calibration gas having a ratio of carrier gas to reference gas;
   the pump being adapted and arranged to pump the volatile reference liquid from the source to the media at a controlled flow rate for controlling the ratio.

2. Apparatus of claim 1, wherein the media is coupled in liquid communication to the source.

3. Apparatus of claim 1 wherein the pump is adjustable for adjusting the flow rate of the volatile reference liquid to the media.

4. Apparatus of claim 1, further including a pump for providing the stream at a desired flow rate.

5. Apparatus of claim 1, further including a baffle chamber for receiving and mixing the calibration gas to rid it substantially of volatile reference gas concentration irregularities.

6. Apparatus of claim 1, wherein the media is formed as a wick element having a stage for receiving the volatile reference liquid and conducting the volatile reference liquid to the wick element.

7. Apparatus of claim 6, wherein the stage is engaged directly to the wick element.

8. Apparatus of claim 6, wherein the wick element comprises an elongate tubular element.

9. Apparatus for generating calibration gas comprising:
   a structure including a chamber containing a porous high surface area media;
   a first pump for pumping a stream of carrier gas through the structure and the chamber;
   a second pump for pumping volatile reference liquid from a source to the media which evaporates therefrom into a reference gas that the stream of carrier gas passing through the chamber absorbs to form a calibration gas having a ratio of carrier gas to reference gas;
   the first pump being adapted and arranged to pump the carrier gas through the chamber at a controlled first flow rate for controlling the ratio; and
   the second pump being adapted and arranged to pump the volatile reference liquid from the source to the media at a controlled second flow rate for controlling the ratio.

10. Apparatus of claim 9, wherein the media is coupled in liquid communication to the source.

11. Apparatus of claim 9, wherein the first pump is adjustable for adjusting the first flow rate.

12. Apparatus of claim 9, wherein the second pump is adjustable for adjusting the second flow rate.

13. Apparatus of claim 9, further including a baffle chamber for receiving and mixing the calibration gas to rid it substantially of volatile reference gas concentration irregularities.

14. Apparatus of claim 9, wherein the media is formed as a wick element having a stage for receiving the volatile reference liquid and conducting the volatile reference liquid to the wick element.

15. Apparatus of claim 14, wherein the stage is engaged directly to the wick element.

16. Apparatus of claim 14, wherein the wick element comprises an elongate tubular element.

17. Apparatus of claim 9, further including a desiccant column of the structure for drying the carrier gas before it enters the chamber.

18. A method of generating calibration gas comprising the steps of:

provid a structure having a chamber containing a porous high surface area media;

passing carrier gas through the chamber;

passing a volatile reference liquid into the media at a flow rate which evaporates therefrom into a reference gas that the stream of carrier gas passing through the chamber absorbs to form a calibration gas having a ratio of carrier gas to reference gas; and varying the flow rate to control the ratio.

19. The method of claim 18, wherein the step of varying further includes the step of increasing the flow rate.

20. The method of claim 18, wherein the step of varying further includes the step of decreasing the flow rate.

21. A method of generating calibration gas comprising the steps of:

providing a structure having a chamber containing a porous high surface area media;

passing a carrier gas through the chamber at a first flow rate;

passing a volatile reference liquid into the media at a second flow rate which evaporates therefrom into a reference gas that the stream of carrier gas passing through the chamber absorbs to form a calibration gas having a ratio of carrier gas to reference gas;

varying the first flow rate to control the ratio; and varying the second flow rate to control the ratio.

22. The method of claim 21, wherein the step of varying the first flow rate further includes the step of increasing the first flow rate.

23. The method of claim 21, wherein the step of varying the first flow rate further includes the step of decreasing the first flow rate.

24. The method of claim 21, wherein the step of varying the second flow rate further includes the step of increasing the second flow rate.

25. The method of claim 21, wherein the step of varying the second flow rate further includes the step of decreasing the second flow rate.

* * * * *